(12) United States Patent
Durrant

(10) Patent No.: US 6,838,054 B1
(45) Date of Patent: Jan. 4, 2005

(54) BIOCHEMICAL DEVICES AND THEIR METHODS OF MANUFACTURE

(75) Inventor: James Robert Durrant, London (GB)

(73) Assignee: Imperial College of Science, Technology and Medicine, London (GB)

( * ) Notice: Subject to any disclaimer, the term of this patent is extended or adjusted under 35 U.S.C. 154(b) by 0 days.

(21) Appl. No.: 09/673,538
(22) PCT Filed: Mar. 31, 1999
(86) PCT No.: PCT/GB99/00999
§ 371 (c)(1),
(2), (4) Date: Feb. 16, 2001
(87) PCT Pub. No.: WO99/54718
PCT Pub. Date: Oct. 28, 1999

(30) Foreign Application Priority Data

Apr. 17, 1998 (GB) ................................. 9808264

(51) Int. Cl.⁷ ............................................. G01N 27/12
(52) U.S. Cl. ................ 422/82.02; 422/90; 422/98; 204/403.01; 204/416; 257/40; 257/642; 356/128; 424/9.1; 424/482; 702/19
(58) Field of Search ............... 257/40, 642; 422/82.02, 422/82.03, 90, 88; 204/400, 403, 416; 356/128; 436/164, 166, 169; 424/9.1, 482; 702/19

(56) References Cited

U.S. PATENT DOCUMENTS 5,364,797 A 11/1994 Olson et al.
5,585,646 A 12/1996 Kossovsky et al.
5,874,047 A 2/1999 Schöning et al.
5,922,537 A * 7/1999 Ewart et al.

FOREIGN PATENT DOCUMENTS

| EP | 0 596 421 | 5/1994 |
| WO | 92/21976 | 12/1992 |
| WO | 96/00198 | 1/1996 |

OTHER PUBLICATIONS

T. Gerfin et al., "Molecular and Supramolecular Surface Modification of Nanocrystalline TiO2 Films: Charge–Separating and Charge–Injecting Devices", Prog. Inorg. Chem. (1997), 44(Molecular Level Artificial Photosynthetic Materials), pp. 345–393.

* cited by examiner

Primary Examiner—Lyle A. Alexander
(74) Attorney, Agent, or Firm—Renner, Otto, Boisselle & Sklar, LLP

(57) ABSTRACT

Biochemical devices comprising a sensing surface that is at least partially covered by a nanocrystalline metal oxide semiconductor film which provides a recipient surface for immobilizing biochemical species on. The film has a mesoporous surface that gives up to a 1000 increase in biochemical species adsorption when compared to a flat surface. The biochemical devices comprising these surfaces can be optical and electrochemical biosensors and reactors for synthetic or biodegradation reactions.

21 Claims, 3 Drawing Sheets

BIOCHEMICAL DEVICES AND THEIR METHODS OF MANUFACTURE

This application is a national phase of International Application No. PCT/GB99/00999, filed on Mar. 31, 1999 and published in English.

This invention relates to biochemical devices such as biosensors and their methods of manufacture.

A wide range of devices used in chemistry and biology (such as in the biotechnological field) require the immobilisation of a biochemical species upon a substrate or film, so that the biochemical species can be sensed or can react with another substance. Such devices include electrochemical, optical and electro-optical bioanalytical devices, and reactors for synthetic or biodegradation reactions. These reactors may be driven optically and/or electrically.

A range of strategies are currently employed for the immobilisation of biochemical species in biochemical devices, the strategy used depending upon the device and its application. For example, an electrochemical biosensor device requires electrical contact between the biochemical species, such as a protein, and a conducting electrode. Procedures employed in optimising this contact include aligning the biochemical species on chemically modified electrodes, attaching electron-transporting groups or modified redox co-factors and immobilising the biochemical in polymer matrices. With optical biosensors, however, optical transparency of the solid substrate is a key issue. In these devices polymeric or silicate glass matrices have been employed to encapsulate the biochemical species. These biosensors are used to detect a wide variety of different things, such as sugars or pH.

In many cases, the immobilisation of the biochemical species is achieved during the process of matrix formation. Such matrix formation requires drying for prolonged periods and/or at elevated temperatures. Such procedures tend to cause denaturisation of many biochemical species, in particular proteins.

WO-A-96/00198 discloses a process for producing ceramic layers including titanium dioxide. These ceramic layers can have enzymes immobilised in them for use in the biochemical field. These layers are produced by mixing a suspension containing $TiO_2$ and an enzyme and then drying it in a stream of warm air at 80° C. Due to the high temperature used in drying this process is only applicable to thermally stable biochemical species. Many biochemical species are not thermally stable.

In accordance with one aspect of the present invention there is provided a biochemical device comprising a surface for immobilising a biochemical species, wherein said surface is at least partially covered with a nanocrystalline metal oxide semiconductor film, said film providing a recipient surface for immobilisation of said biochemical species.

Thus the present invention alleviates the disadvantages of the prior art by the use of nanocrystalline metal oxide semiconductor films. These films typically comprise nanometer-sized crystalline particles (typical diameter 5–50 nm) which are densely packed to form a mesoporous structure with a surface area up to 1000 times greater than its geometrical area.

In other words, in embodiments of the invention a biomolecule can be immobilised on a preformed, mesoporous film, in contrast to previous techniques of matrix immobilisation where film formation and biomolecule immobilisation are achieved in a single process. This allows the immobilisation to be conducted under conditions which do not denature the protein or other biomolecule, of which the use of lower temperatures is one important example. This combination of mild immobilisation conditions and the specific properties of the film (high biomolecule loading, optical transparency, stability, electrical conductivity) are technical advantages of this invention.

Furthermore, these nanocrystalline metal oxide semiconductor films have simple and flexible biochemical attachment chemistries. Attachment may occur covalently, by adsorption, by bio-derivitisation of the film or by combinations thereof.

Nanocrystalline metal oxide semiconductor films combine a high surface area and excellent stability with efficient current transport In addition to a high surface area these substances have rapid diffusion paths due to the pores being larger than the biochemical species, and this in turn allows the rapid mass transport of the analyte into and through the film. Furthermore, their high surface area to geometrical area enables a small device to hold a large quantity of the biochemical species. This enables the size of the device to be decreased resulting in increased mass transport giving faster response times. Additionally a smaller device has the practical advantage of being able to be used in restricted volumes. Furthermore, the high loading of the biochemical molecules makes them less susceptible to loss of activity. No existing materials employed for biochemical applications exhibit all of these properties.

In a preferred embodiment the nanocrystalline metal oxide semiconductor is titanium dioxide, $TiO_2$. $TiO_2$ has a wide band gap and as such is optically transparent, making it suitable for optical applications as well as electrical ones.

In further embodiments the nanocrystalline metal oxide semiconductor is zinc oxide, ZnO or zirconium dioxide, $ZrO_2$.

In one embodiment a biochemical species is immobilised on at least a portion of the film. Preferably, the biochemical species is a protein. The term protein, when used in this application should be taken to include enzymes, antibodies or fragments thereof and other polypeptides capable of binding molecules or catalysing their transformation to another molecular species.

In a further embodiment attachment of the biochemical species occurs by bio-derivitisation of the film. Bio-derivitisation of the film involves using a chemical species —such as a biomolecule—as an intermediary, the biochemical species molecule becoming immobilised to the film via the chemical species—i.e. the biochemical species is bound to the chemical species which is in turn bound to the film. This has the advantage of increasing the number of possible biochemical species that can be immobilised by the film, and improving the stability of immobilisation. An example of this is the use of the enzyme avidin. Avidin is expected to bind strongly to $TiO_2$ due to its positive charge. Any biomolecule with a biotin group attached (readily added) can bind to avidin.

In a further embodiment the biochemical device is a biosensor. The nanocrystalline metal oxide semiconductor film providing an ideal surface for inmmobilising a sensing biochemical species for use in such a device.

Advantageously, the film forms an array on the surface. A conveniently shaped sensing area can thus be formed. Furthermore, the array allows for different sensing biochemical species to be attached to different portions of the array. Thus a variety of substances can be detected and depending on the biochemical species used, both electrochemical and optical signals may be produced. These arrays may be simply and accurately produced by screen printing or other method compatible with the properties of the substance being deposited.

In a preferred embodiment a pH sensitive dye is additionally attached to a further portion of the film. Thus changes in the sample pH can be monitored optically and the results can be used to correct for pH effects on, for example, an enzyme-based sensing element.

In one embodiment the biosensor is an electrochemical biosensor, comprising an electrical circuit connected to the film, the circuit comprising a meter for monitoring changes in the current, voltage, conductivity or impedance in the circuit produced by an electrochemical reaction. The conductive nature of the film makes it especially suited to such a device.

In a further embodiment the biosensor comprises an optical sensor that acts to optically detect substances, by monitoring the interaction of electromagnetic radiation with the molecules present. The transparent nature of many metal oxide semiconductor films makes them particularly suited to such an application. In preferred embodiments the immobilised biochemical species is a fluorescent labelled or fluorophore labelled biochemical species and it is the fluorescence thus produced that provides an indication of the concentration of the substance under investigation. Control electronics form part of the device and are used to calculate the concentration. Alternatively, the fluorescence may arise from the binding of a fluorescent molecule to a biochemical species already on the surface. Fluorescence may also be generated by the formation of a fluorescent product from a non-fluorescent substrate through an enzymatic reaction.

In one embodiment the device comprises both an electrochemical biosensor and an optical one, such that a plurality of substances may be detected by the one sensor. The conductive and transparent nature of the film makes it particularly suitable for use in such a dual purpose environment.

In a further preferred embodiment the sensing biochemical species can be electrochemically or photochemically switched to a reactive state by oxidation or reduction or through the production of small molecules or ions e.g. $H^+$. This allows the sensing element in the device to be regenerated by switching the direction of the electric current after optical sensing. Furthermore, where there are concerns about the stability of the sensing molecule the current measured during the electrochemical regeneration step would be an indication of the amount of active material present and so give an opportunity for recalibration.

In a preferred embodiment the biosensor comprises a photoelectric element or other power generating element such that the biosensor can be used in remote areas, for military applications and for long term sensing, with data being sent by telemetry. Advantageously the photoelectric element may be a portion of the $TiO_2$ film, its photovoltaic properties acting to produce the necessary power.

In a further embodiment the biochemical device is a reactor for synthetic, catalytic or biodegradation reactions. The film provides a suitable site for immobilising biochemical species, in particular, enzymes involved in the reaction. In one embodiment the device comprises an electrical source for electrically driving the reaction, the electrical conductivity of the film making it particularly suitable for such an arrangement In another embodiment the biochemical device comprises an optical source, the reaction being driven optically. The transparent nature of many nanocrystalline metal oxide semiconductor films makes them particularly suited to such an application.

In a preferred embodiment the biochemical reactor comprises a photoelectric element for producing the reaction driving current. Advantageously the nanocrystalline metal oxide semiconductor film may be $TiO_2$, and the photoelectric element may be a portion of that $TiO_2$ film, its photovoltaic properties acting to produce a photoelectric current.

In some embodiments the reaction may be optically driven, the biochemical device being arranged to receive electromagnetic radiation, possibly by the provision of optically transparent windows in the outer casing of the biochemical device. Alternatively, the biochemical device may include a light source.

In accordance with another aspect of the present invention there is provided a method of manufacturing a biochemical device, comprising covering at least a portion of a sensing surface with a film of nanocrystalline semiconductor, contacting said film with a biochemical species such that said biochemical species is immobilised onto said film. The immobilisation is preferably achieved after fabrication of the semiconductor film, under conditions which may be selected to minimise or at least reduce degradation/denaturisation of the biochemical species.

Preferably, the film is applied by screen printing followed by sinteting in air. Nanocrystalline metal oxide semiconductors are particularly suited to screen printing as they form colloidal suspensions. Screen printing is a well established and cheap technology providing films from low cost precursors. Such means of fabrication also enables robust films of the material to be deposited in various patterns.

In some embodiments the biochemical species are caused to contact the preformed film by immersing said at least partially covered sensing surface into an aqueous solution of a biochemical species such that said biochemical species is immobilised onto said film. This immobilisation may be achieved without the use of non-physiological temperatures, pH and solvents.

The generic nature of the immobilisation chemistry onto the nanocrystalline material, in particular through adsorption or covalent attachment, means the deposition of the biochemical species can advantageously be done using a commercially available "gridding robot". This is an instrument which allows volumes of liquids to be dispensed at specified x-y co-ordinates. Different liquids (e.g. biomolecules in solution) can be dispensed in an arbitrary pattern. The advantage is that once the pattern of sensing elements has been laid down by printing the biomolecules can be patterned on top using the robot. In alternative embodiments other deposition methods such as ink jet printing may be used.

In preferred embodiments the temperature at which the film is contacted with the biochemical species is 4° C., in order to optimise stability of the biochemical species.

In some embodiments the biochemical species is a protein.

Embodiments of the present invention will now be described, by way of example only, and with reference to the accompanying drawings, in which:

BRIEF DESCRIPTION OF THE DRAWINGS

FIG. 1 illustrates a fluorescent biosensor for sensing the presence of maltose. The biosensor comprises a substrate 10 which is covered by a film 20 of TiO$_2$ with a IANBD (4-[N-(2-(iodoacetoxy)ethyl)-N-methylamino]-7-nitobenz-2oxa-1,3diazole) labelled Maltose Binding Protein MBP) immobilised on it, a container for holding the solution 30 under investigation, a light source 40, a fluorescence detector 50 and control electronics.

The coated substrate was produced by screen printing a 10μm thick nanocrystalline TiO$_2$ film onto the substrate using a colloidal suspension of TiO$_2$, and then immersing the substrate in an aqueous solution of a IANBD labelled Maltose Binding Protein (MBP) at 4° C. This results in an approximate monolayer coverage of the film with MBP. This coverage is up to a 1000 fold increase in adsorption relative to a flat surface due to the mesoporous structure of the film.

The biosensor operates by immersing the MBP covered substrate in the solution 30 under investigation. Any maltose present in the solution will bind to the MBP thereby increasing the fluorescence of the label by up to 200%. The substrate is illuminated by a light source 40 at an appropriate wavelength and the fluorescence is detected by a fluorescence detector 50, the detection being aided by the optical transparency of the film. Control electronics 60 calculate the amount of maltose present in the solution from the fluorescence detected, and output the result.

Alternatively, the, generic nature of the immobilisation chemistry onto the nanocrystalline material, in particular through adsorption or covalent attachment, means the deposition of the biochemical species can advantageously be done using a commercially available "gridding robot". This is an instrument which allows volumes of liquids to be dispensed at specified x-y co-ordinates, Different liquids (e.g. biomolecules in solution) can be dispensed in an arbitrary pattern. The advantage is that once the pattern of sensing elements has been laid down by printing the biomolecules can be patterned on top using the robot. In alternative embodiments other deposition methods such as ink jet printing may be used.

In other embodiments, a fluorophore-labelled species could be used.

Figure 1:
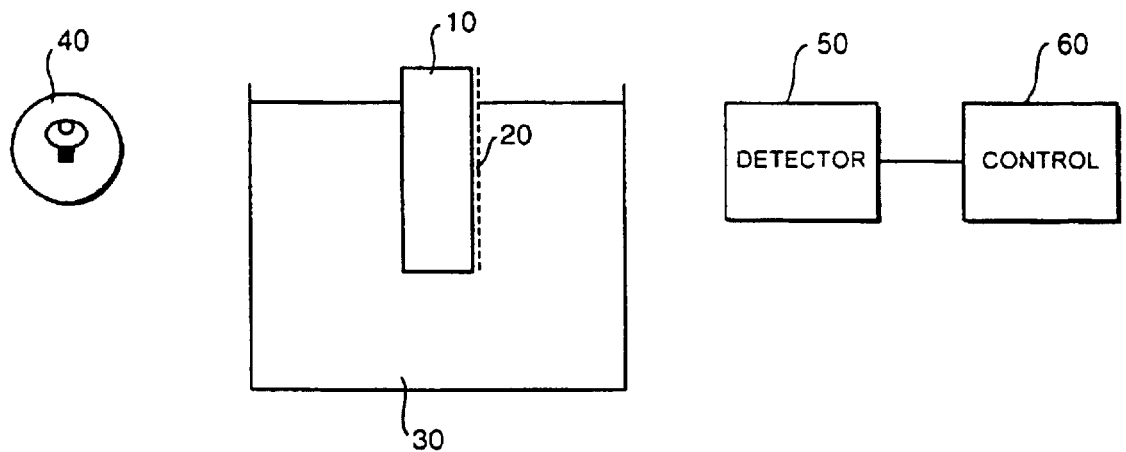
FIG. 1 illustrates a biosensor according to an embodiment of the present invention.
Figure 2:
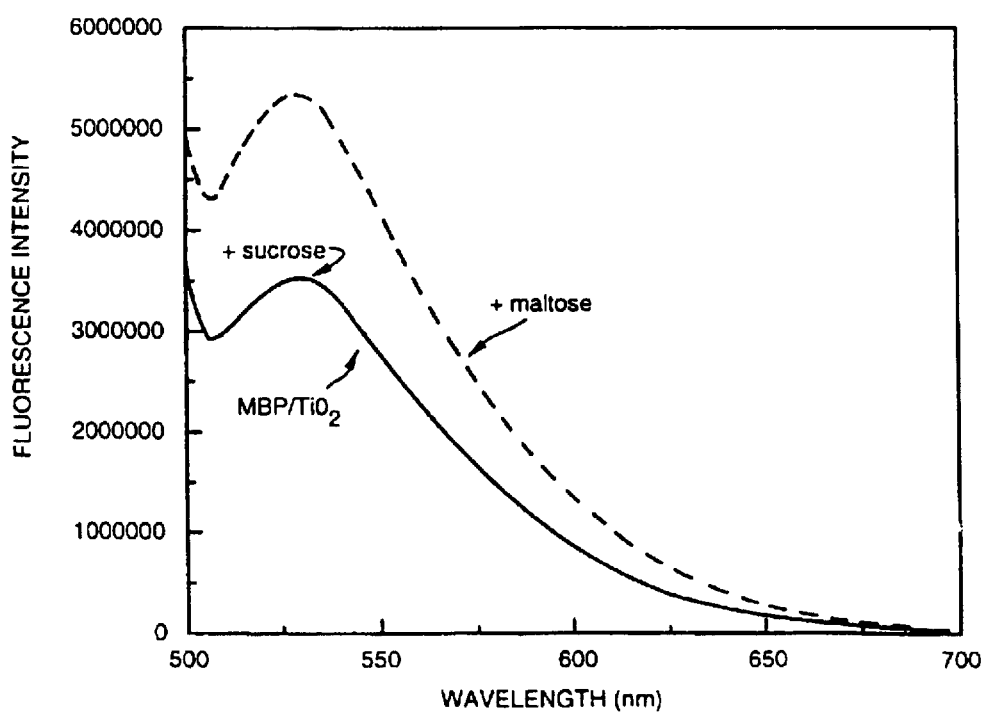
FIG. 2 illustrates the fluorescent emission spectra of IANBD labelled maltose binding protein coated $TiO_2$ films immersed in maltose and sucrose solutions.

FIG. 2 illustrates the results produced by the device illustrated in FIG. 1, for a solution containing 500 μM maltose and one containing sucrose. As expected the solution containing maltose causes the fluorescence intensity to increase, whereas the control solution containing only sucrose shows no change in fluorescence intensity.

Figure 3:
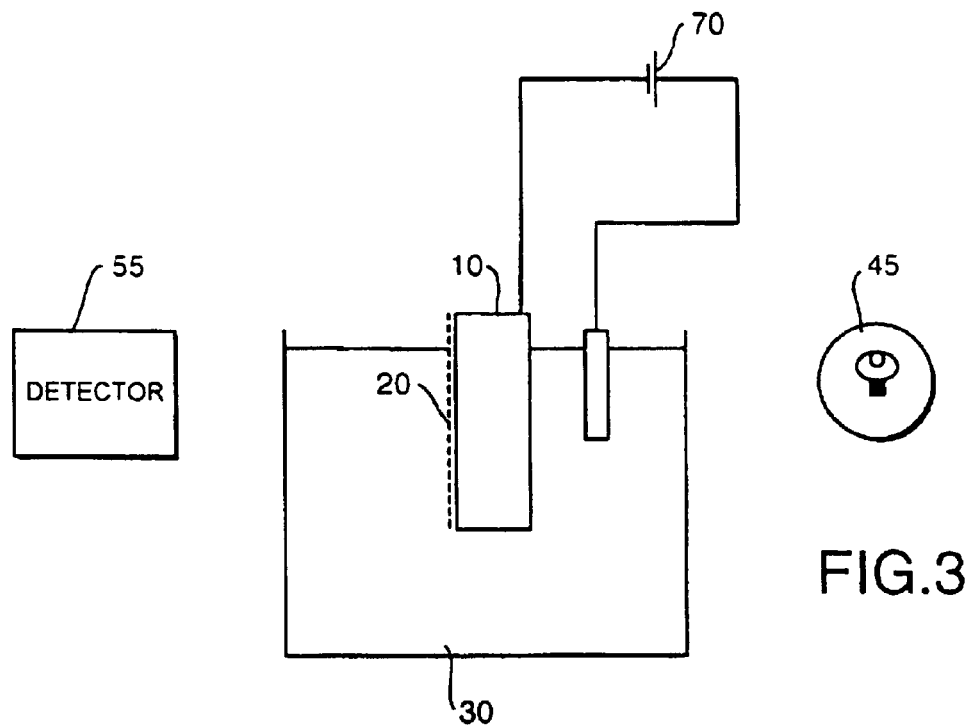
FIG. 3 illustrates an electro-optical biosensor.

FIG. 3 illustrates an electro-optical biosensor, comprising a substrate 10 which is covered by a film 20 of TiO$_2$ with cytochrome c immobilised on it. The substrate is connected to a variable voltage supply 70. An absorption spectrometer is shown schematically as a light source 45 and a detector 55, but the actual implementation of such a spectrometer to provide an absorption spectrum through the biosensor is well known in the art. A detector can be connected in the circuit to monitor chances in the current and/or voltage in the circuit produced by an electrochemical reaction taking place.

Figure 4:
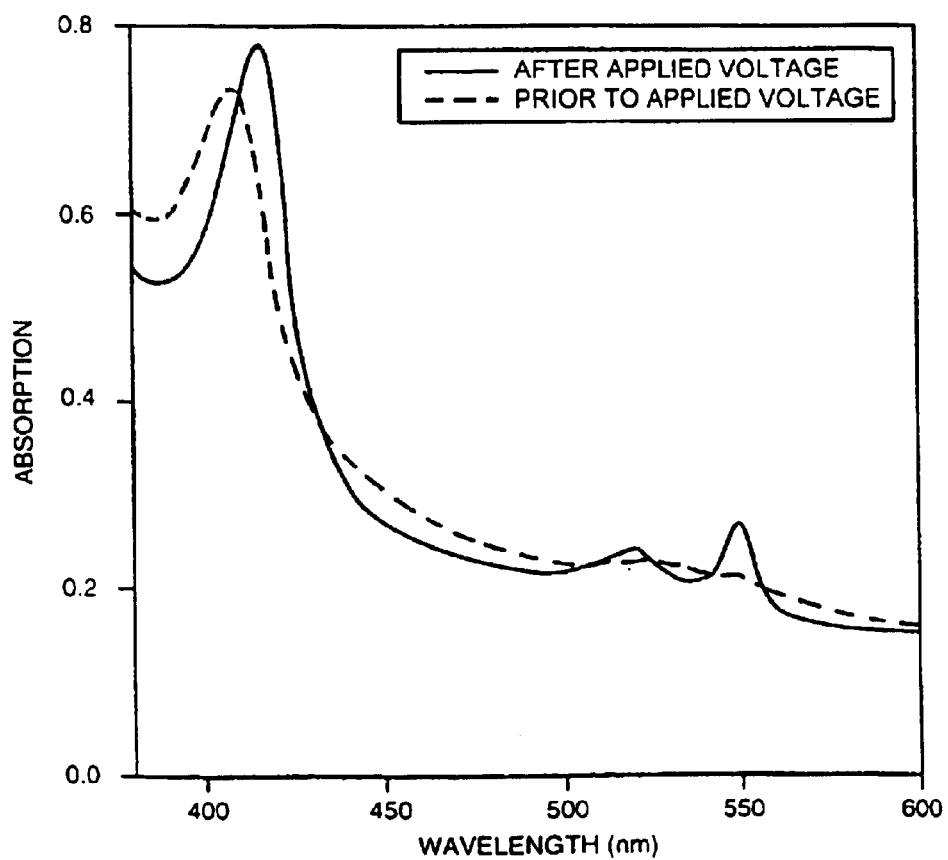
FIG. 4 illustrates absorption spectra of cytochrome c coated $TiO_2$ films before and after application of −0.6V vs Ag/Ag cl (reference electrode)

The absorption spectra illustrated in FIG. 4 are produced by the device illustrated in FIG. 3. The two spectra are produced by the cytochrome c before and after the application of –0.6V to the back surface of the substrate respectively. The cytochrome c protein was immobilised on the TiO$_2$ coated substrate by immersion of the substrate in an aqueous solution of cytochrome c at 4° C.

FIG. 4 shows changes in the characteristic reduction of the cytochrome c with applied voltage and it is therefore clear that there is electrical connectivity between the external circuit and the adsorbed protein. These results thereby demonstrate the suitability of a substrate coated with a TiO$_2$ film for use in an electrochemical biosensor.

Furthermore, such a biosensor can be electrochemically switched to a reactive state by an applied voltage that aids oxidation or reduction. This allows the sensing element in the device to be regenerated by switching the direction of the electric current after optical sensing. It has further been demonstrated that the immobilised cytochrome c may be reduced by ultraviolet illumination. Illumation was achieved by 337 nm pulses from a nitrogen laser, resulting in band gap excitation of the TiO$_2$ film. Thus the redox states of immobilised proteins may be modulated by electromagnetic illumination, resulting from either a separate photoelectric element or from solar irradiation. Thus the sensing element in the device may be regenerated by either electrical current or electromagnetic irradiation. Such reduction/oxidation of the biomolecule is also applicable to the function of electrocatalytic/photocatalytic biochemical devices for synthetic, bioremediation and other biotechnological applications.

Figure 5:
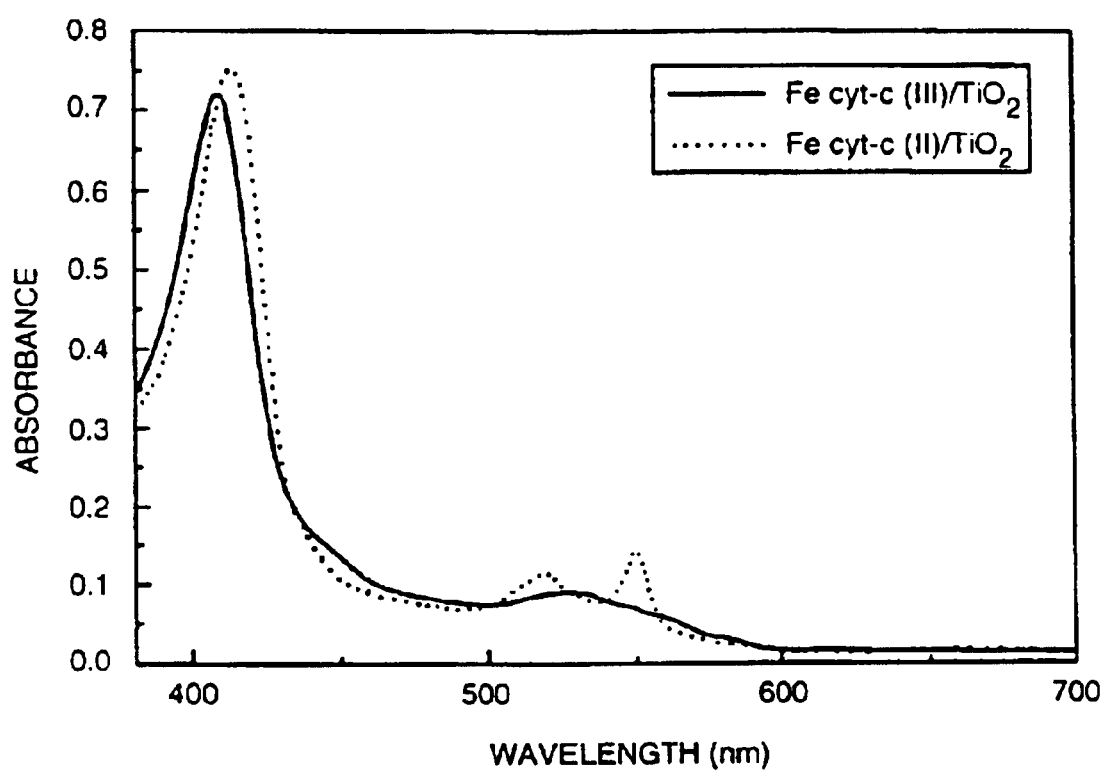
FIG. 5 illustrates photochemical reduction of cytochrome-c showing absorption spectra of cytochrome C/TiO$_2$ films before (–) and after ( . . . . ) ultraviolet illumination of the film.

FIG. 5 illustrates the photochemical reduction of Fe(III) Cyt-c to Fe(II) Cyt-c driven by 337 nm bandgap excitation of the TiO$_2$. This reduction is attributed to photoinduced electron transfer from the conduction band of the TiO$_2$ to the immobilised protein. This demonstrates that TiO$_2$/ biomolecule devices arranged for synthetic/catalytic/biodegradation reactions can be driven optically as well as electrically. This photochemical reduction (or, in principle oxidation) could also be used to regenerate the sensing state during biosensor function.

Table 1, below, gives a summary of some of the proteins that have been successfully immobilised on TiO$_2$ nanoporous films.

TABLE 1

| Protein | Source | Activity | Comments | Activity |
|---|---|---|---|---|
| Cytochrome c | Mammalian | Electron transfer | Electrochemically coupled to TiO$_2$ | ✓ |
| Maltose binding protein | Bacteria (recombinant) | ligand binding | Ligand binding detected by fluorescence | ✓ |
| Cytochrome c peroxidase | Yeast (recombinant) | Hydrogen peroxide reduction | | Not tested |
| Haemoglobin | Mammalian | O$_2$ binding | Electrochemically coupled to TiO$_2$. Can be used as an NO sensor. | ✓ |
| Alkaline | Bacteria | Hydrolysis of | Activity measured by | ✓ |

TABLE 1-continued

| Protein | Source | Activity | Comments | Activity |
| --- | --- | --- | --- | --- |
| phosphatase | (recombinant) | Phosphate esters | fluorescence. Both wild-type and "his tag" proteins can be immobilised. The latter after $Ni^{2+}$ treatment | |
| Horseradish peroxidase | Plant | Substrate oxidation | Activity measure by absorbance | ✓ |

The above examples illustrate a key advantage of using a substrate coated with a $TiO_2$ film, namely that immobilisation of the biochemical species is achieved at 4° C., thereby reducing the risks of denaturisation. Another advantage of using a $TiO_2$ film is that in some embodiments a portion of the film may be used as a photoelectric element, allowing the device to be used in remote locations without a separate power source.

In other embodiments of the present invention other nanocrystalline semiconductor films, such as ZnO or ZrO are used.

In further embodiments the nanocrystalline metal oxide semiconductor film is in the form of an array which is screen printed onto the surface. Different biochemical species may be attached to different portions of the array and in some embodiments a pH sensitive dye is also applied to the surface.

Other embodiments of the present invention include the use of nanocrystalline semiconductor metal oxide films in reactors for synthetic or biodegradation reactions. These reactors can be electrically or optically driven.

In further embodiments a pH sensitive dye is additionally attached to a further portion of the film. Thus changes in the sample pH can be monitored optically and the results can be used to correct for pH effects on, for example, an enzyme-based sensing element.

It will be apparent, of course, that the present invention has been described above by way of example only and that modifications may be made within the scope of the appended claims.

What is claimed is:

1. A biosensor for detecting an analyte of interest, comprising a surface, a preformed nanocrystalline metal oxide semiconductor film at least partially covering said surface and at least one temperature-sensitive protein that would be denatured if subjected to non-physiological temperatures immobilized on at least a portion of said preformed film without the use of non-physiological temperatures, such that the biosensor will detect the analyte.

2. A biosensor according to claim 1, wherein said nanocrystalline metal oxide is titanium dioxide.

3. A biosensor according to claim 1, wherein said nanocrystalline metal oxide is zinc oxide.

4. A biosensor according to claim 1, wherein said nanocrystalline metal oxide is zirconium dioxide.

5. A biosensor according to claim 1, wherein said film is a bioderivitised film to which said at least one protein is immobilised.

6. A biosensor according to claim 1, wherein said film forms an array on said surface.

7. A biosensor according to claim 6, wherein different proteins are bound to different portions of said array.

8. A biosensor for detecting an analyte of interest, comprising a surface, a nanocrystalline metal oxide semiconductor film at least partially covering said surface and at least one protein immobilized on at least a portion of said film without the use of non-physiological temperatures, such that the biosensor will detect the analyte, and further comprising a pH-sensitive dye partially covering said surface.

9. A biosensor according to claim 1, wherein said biosensor is an electrochemical biosensor, and further comprising an electrical circuit electrically connected to said film, said circuit comprising a detector for monitoring changes in the current or voltage in said circuit produced by an electrochemical reaction.

10. A biosensor according to claim 1, wherein said biosensor is an optical biosensor, and further comprising an optical sensor for monitoring a reaction by sensing the interaction of electromagnetic radiation with the molecules present.

11. An optical biosensor according to claim 10, wherein said at least one protein is a fluorescent or fluorophore labelled protein, said film is optically transparent, and further comprising a light source and control electronics for calculating concentrations from the output of said optical sensor.

12. A biosensor according to claim 1, further comprising an electrical circuit electrically connected to said film, and an optical sensor.

13. A biosensor according to claim 12, wherein said at least one protein is such as to be electrochemically or photochemically switched to a sensing state by oxidation or reduction, the results of the sensing reaction being measured optically or electrically.

14. A biosensor according to claim 1, wherein said biosensor further comprises a power supplying element.

15. A biosensor according to claim 14, wherein said power supplying element comprises a photoelectric element operable to supply power in response to electromagnetic radiation.

16. A biosensor according to claim 15, wherein a portion of said film forms said photoelectric element.

17. A method of manufacturing a biosensor for detecting an analyte of interest, comprising the steps of covering at least a portion of a surface with a film of a nanocrystalline metal oxide semiconductor, contacting said preformed film with at least one temperature sensitive protein that would be denatured if subjected to non-physiological temperatures, to immobilize said protein on said preformed film without the use of non-physiological temperatures, such that the biosensor will be operative to detect the analyte.

18. A method of manufacturing a biosensor according to claim 17, wherein said film is applied to said surface by screen printing.

19. A method of manufacturing a biosensor according to claim 17, wherein said film is contacted with a protein by immersion of said at least partially covered surface in an aqueous solution of said protein.

20. A method of manufacturing a biosensor according to claim 17, wherein said protein is deposited on said film using a gridding robot or other dispensing device such as an ink-jet printer.

21. A method of manufacturing a biosensor according to claim 17, wherein the temperature at which said film is contacted with said protein is substantially 4° C.

* * * * *

UNITED STATES PATENT AND TRADEMARK OFFICE
CERTIFICATE OF CORRECTION

PATENT NO. : 6,838,054 B1
DATED : January 4, 2005
INVENTOR(S) : Durrant et al.

It is certified that error appears in the above-identified patent and that said Letters Patent is hereby corrected as shown below:

Title page,
Item [75], Inventors, after "James Robert Durrant, London (GB)" add the names:
-- Anthony Edward George Cass, London (GB);
Gianfranco Gilardi, London (GB) --

Signed and Sealed this

Nineteenth Day of July, 2005

JON W. DUDAS
*Director of the United States Patent and Trademark Office*